(12) United States Patent
Shen et al.

(10) Patent No.: US 11,547,350 B2
(45) Date of Patent: Jan. 10, 2023

(54) PERSONALIZED PARAMETER LEARNING METHOD, SLEEP-AID DEVICE AND NON-TRANSITORY COMPUTER READABLE MEDIUM

(71) Applicant: INDUSTRIAL TECHNOLOGY RESEARCH INSTITUTE, Hsinchu (TW)

(72) Inventors: Chih-Tsung Shen, Chiayi (TW);
Hsin-Jung Cheng, Kaohsiung (TW);
Ching-Hao Lai, Taichung (TW);
Szu-Han Tzao, Taoyuan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 1050 days.

(21) Appl. No.: 16/232,400

(22) Filed: Dec. 26, 2018

(65) Prior Publication Data

US 2020/0205727 A1 Jul. 2, 2020

(51) Int. Cl.
*A61B 5/00* (2006.01)
*A61M 21/02* (2006.01)
*A61M 21/00* (2006.01)

(52) U.S. Cl.
CPC .......... *A61B 5/4815* (2013.01); *A61B 5/4809* (2013.01); *A61M 21/02* (2013.01);
(Continued)

(58) Field of Classification Search
CPC ...... A61B 5/4815; A61B 5/4809; A61M 1/02; A61M 2021/0027; A61M 2021/0044
(Continued)

(56) References Cited

U.S. PATENT DOCUMENTS 8,348,840 B2 1/2013 Heit et al.
9,474,876 B1 * 10/2016 Kahn .................... A61M 21/02
(Continued)

FOREIGN PATENT DOCUMENTS

CN 103648221 A 3/2014
CN 103780691 A 5/2014
(Continued)

OTHER PUBLICATIONS

Chinese Office Action and Search Report for Chinese Application No. 201910316313.4, dated Jul. 2, 2021.
(Continued)

*Primary Examiner* — Michael Tomaszewski
(74) *Attorney, Agent, or Firm* — Birch, Stewart, Kolasch & Birch, LLP

(57) ABSTRACT

A personalized parameter learning method, a sleep-aid device and a non-transitory computer readable medium are provided. The personalized parameter learning method for a sleep-aid device is provided. The personalized parameter learning method includes the following steps. A process device computes a measured sleep quality of a user after operating a sleep-aid device with an inputted parameter setting at least according to a subjective feedback from the user. The processing device generates a plurality of candidate parameter settings according to the measured sleep quality. The processing device generates a plurality of predicting sleep qualities corresponding the candidate parameter settings. The processing device obtains a recommending parameter setting by selecting one of the candidate parameter settings according to the predicting sleep qualities.

15 Claims, 4 Drawing Sheets

(52) U.S. Cl.
CPC ............... *A61M 2021/0027* (2013.01); *A61M 2021/0044* (2013.01)

(58) Field of Classification Search
USPC ............................................ 706/12; 705/2–3
See application file for complete search history.

(56) References Cited

U.S. PATENT DOCUMENTS

| | | | |
|---|---|---|---|
| 9,566,410 B2 | 2/2017 | Chang et al. | |
| 2010/0041965 A1* | 2/2010 | Kang | A61B 5/00 600/301 |
| 2011/0230790 A1* | 9/2011 | Kozlov | G04G 13/026 600/595 |
| 2014/0275741 A1* | 9/2014 | Vandenbelt | A61M 21/02 600/26 |
| 2015/0217082 A1* | 8/2015 | Kang | G16Z 99/00 600/27 |
| 2016/0015314 A1* | 1/2016 | Dusanter | A61B 5/4818 600/301 |
| 2016/0015315 A1* | 1/2016 | Auphan | A61B 5/7435 600/587 |
| 2016/0151603 A1 | 6/2016 | Shouldice et al. | |
| 2018/0140228 A1 | 5/2018 | Olivier | |
| 2019/0217048 A1* | 7/2019 | Mlodyszewski | A61M 21/02 |

FOREIGN PATENT DOCUMENTS

| | | |
|---|---|---|
| CN | 104127947 A | 11/2014 |
| CN | 104780831 A | 7/2015 |
| CN | 205964014 U | 2/2017 |
| CN | 106999049 A | 8/2017 |
| CN | 107174209 A | 9/2017 |
| CN | 107670158 A | 2/2018 |
| CN | 107788976 A | 3/2018 |
| CN | 107921261 A | 4/2018 |
| CN | 109008503 A | 12/2018 |
| TW | M524970 U | 7/2016 |
| TW | I559948 B | 12/2016 |
| TW | 201815347 A | 5/2018 |
| TW | 201817423 A | 5/2018 |
| TW | M561462 U | 6/2018 |

OTHER PUBLICATIONS

Chinese Office Action and Search Report for corresponding Chinese Application No. 201910316813.4, dated Mar. 30, 2022.

Taiwanese Office Action and Search Report for Taiwanese Application No. 108111041, dated Oct. 4, 2019.

Harvey et al., "The Subjective Meaning of Sleep Quality: A Comparison of Individuals with and without Insomnia", Sleep, vol. 31, No. 3, 2008, p. 383-393.

\* cited by examiner

PERSONALIZED PARAMETER LEARNING METHOD, SLEEP-AID DEVICE AND NON-TRANSITORY COMPUTER READABLE MEDIUM

TECHNICAL FIELD

The disclosure relates in general to a personalized parameter learning method, a sleep-aid device and a non-transitory computer readable medium.

BACKGROUND

Good sleep quality contributes to the health of the body. Studies have found that adjustments in sound, lighting and other factors contribute to the improvement of sleep quality. Therefore, a sleep-aid technique has been developed.

In the sleep-aid technology, the user can manually adjust the parameters of a sleep-aid device to control the sound and the light. However, each person's physiological clock is different and his physiological condition is different. How to set the appropriate personalized parameters becomes a major bottleneck in the sleep-aid technology.

SUMMARY

The disclosure is directed to a personalized parameter learning method, a sleep-aid device and a non-transitory computer readable medium.

According to one embodiment, a personalized parameter learning method for a sleep-aid device is provided. The personalized parameter learning method includes the following steps. A processing device computes a measured sleep quality of a user after operating a sleep-aid device with an inputted parameter setting at least according to a subjective feedback from the user. The processing device generates a plurality of candidate parameter settings according to the measured sleep quality. The processing device generates a plurality of predicting sleep qualities corresponding the candidate parameter settings. The processing device obtains a recommending parameter setting by selecting one of the candidate parameter settings according to the predicting sleep qualities.

According to another embodiment, a sleep-aid device is provided. The sleep-aid device includes a processing device. The includes a computing module, a parameter learning module and a sleep quality predicting module. The computing module is for computing a measured sleep quality of a user after operating a sleep-aid device with an inputted parameter setting at least according to a subjective feedback from the user. The parameter learning module is for generating a plurality of candidate parameter settings according to the measured sleep quality. The sleep quality predicting module is for generating a plurality of predicting sleep qualities corresponding the candidate parameter settings are generated. the parameter learning module is further obtaining a recommending parameter setting by selecting one of the candidate parameter settings according to the predicting sleep qualities.

According to an alternative embodiment, a non-transitory computer readable medium storing a program causing a computer to execute a personalized parameter learning method. The personalized parameter learning method includes the following steps. A measured sleep quality of a user after operating a sleep-aid device with an inputted parameter setting is computed at least according to a subjective feedback from the user. A plurality of candidate parameter settings are generated according to the measured sleep quality. A plurality of predicting sleep qualities corresponding the candidate parameter settings are generated. A recommending parameter setting is obtained by selecting one of the candidate parameter settings according to the predicting sleep qualities.

Figure 1:
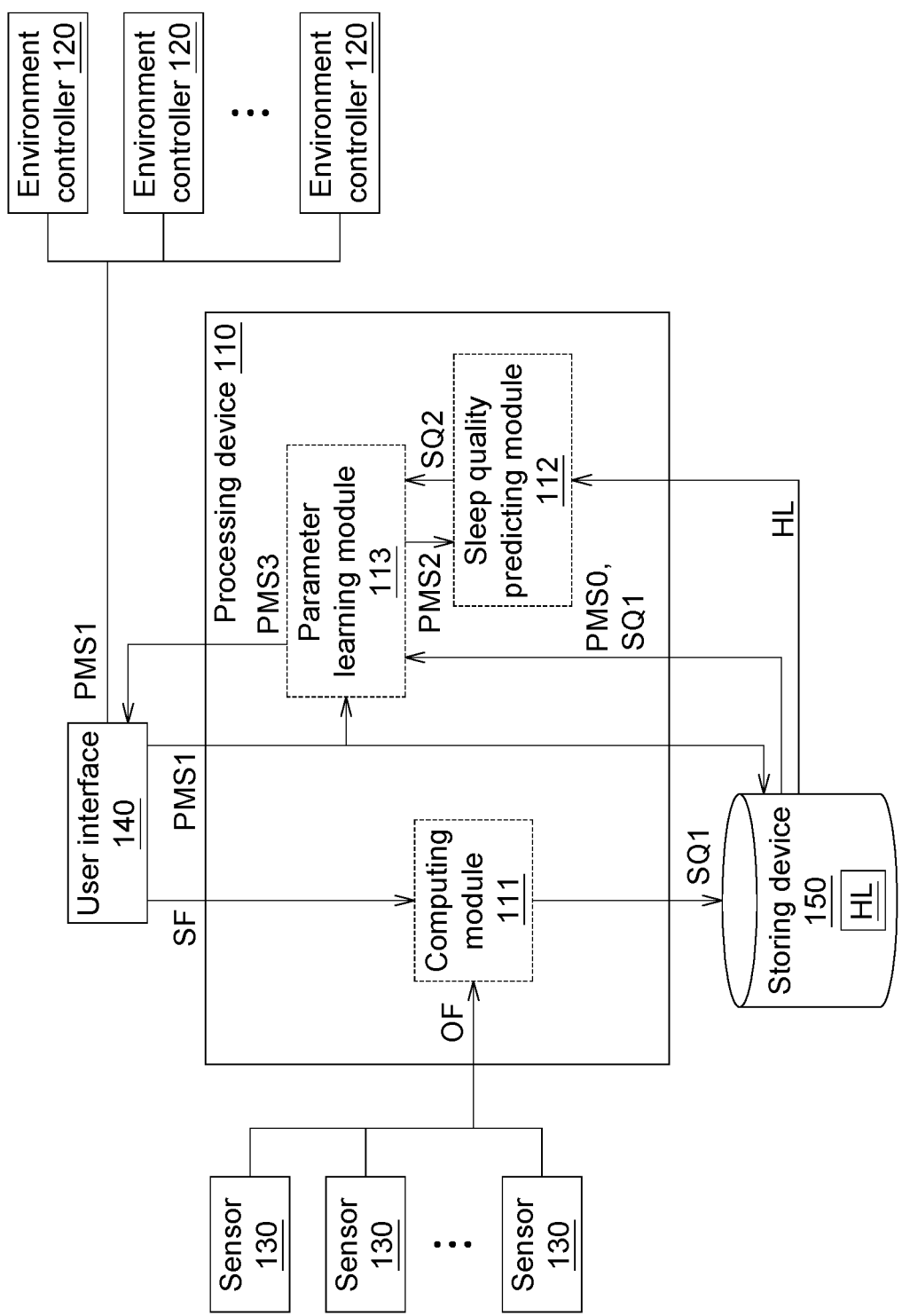
FIG. 1 shows a sleep-aid device according to one embodiment in the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

In the following embodiments, a personalized parameter learning method for a sleep-aid device is provided. In the personalized parameter learning method, an enhanced learning algorithm is used to obtain a recommending parameter setting, such that the sleep quality can be improved.

Please refer to FIG. 1 which shows a sleep-aid device 100 according to one embodiment in the present disclosure. The sleep-aid device 100 may be a smart phone, a bedside lamp, a smart home appliance or a smart remote controller. For example, the sleep-aid device 100 may include a processing device 110, a plurality of environment controllers 120, a plurality of sensors 130, a user interface 140 and a storing device 150. The environment controller 120 may be a speaker controller, a light source controller, an air conditioner controller or an air purifier controller. The sensor 130 may be a wearable device, a voice recorder, a camera or a heartbeat sensor. The user interface 140 may be a touch panel, a microphone or a keyboard. The storing device 150 may be a hard disk, a memory or a cloud storing center.

In the processing device 110, a computing module 111, a sleep quality predicting module 112 and a parameter learning module 113 are used to perform the personalized parameter learning method. Each of the computing module 111, the sleep quality predicting module 112 and the parameter learning module 113 may be a program code module, a firmware or a chip. The operation of those elements is illustrated via a flowchart.

Figure 2:
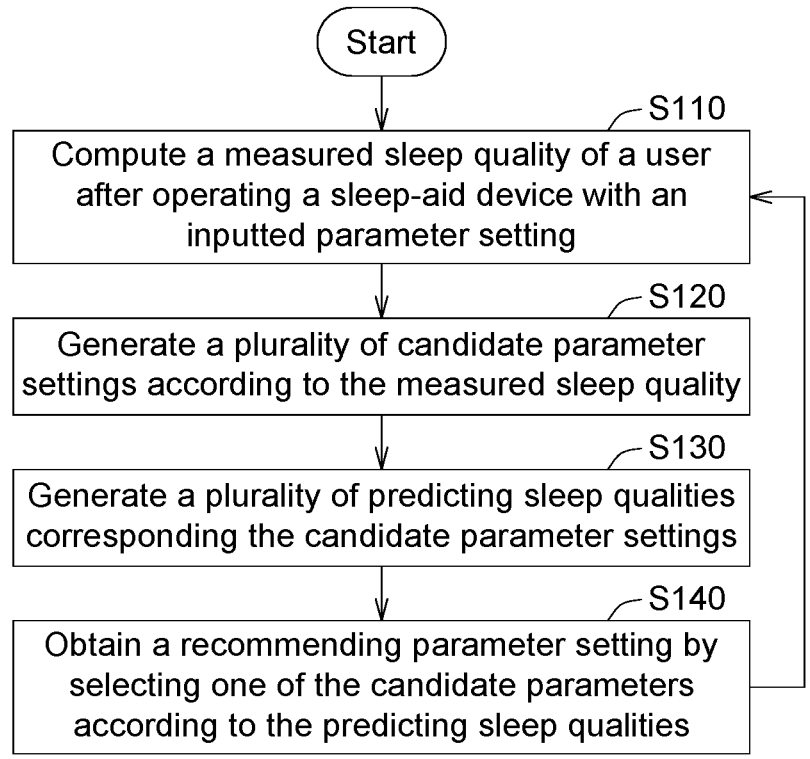
FIG. 2 shows a flowchart of a personalized parameter learning method according to one embodiment in the present disclosure.

Please refer to FIG. 2, which shows a flowchart of the personalized parameter learning method according to one embodiment in the present disclosure. In one embodiment, a non-transitory computer readable medium may store a program causing a computer to execute the personalized parameter learning method. In step S110, the computing module 111 of the processing device 110 computes a measured sleep quality SQ1 of a user after operating the sleep-aid device 100 with an inputted parameter setting PMS1. In one embodiment, the measured sleep quality SQ1 may be computed according to a subjective feedback SF inputted from the user through the user interface 140. For example, please refer to FIG. 3, which shows the user interface 140 according to one embodiment in the present disclosure. In the user interface 140, five stars are shown for being selected. The user may select some of the stars to input the subjective feedback SF.

Or, in another embodiment, the measured sleep quality SQ1 may be computed according to both of the subjective feedback SF and an objective feedback OF form the sensors 130. The objective feedback OF may be the snoring or the heart rate. The subjective feedback SF is obtained according to the actual feeling of the user; the objective feedback OF is obtained according to the measurement results of the user.

Figure 3:
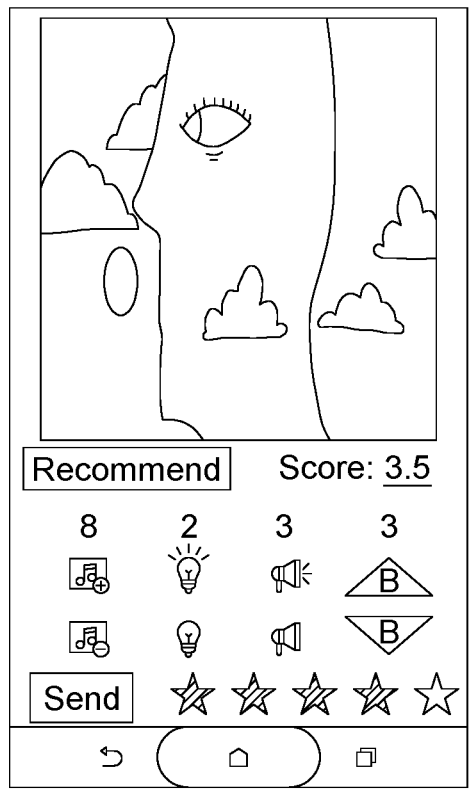
FIG. 3 shows a user interface according to one embodiment in the present disclosure.

In the step S110, the subjective feedback SF is used to compute the measured sleep quality SQ1. For the same inputted parameter setting PMS1, the measured sleep qualities SQ1 of different users may be different due to the different subjective feedbacks SF. Therefore, the score of the measured sleep quality SQ1 can accurately represent the user's personal feelings. A history list HL recording the relationship between the inputted parameter setting PMS1 and the measured sleep quality SQ1 is stored in the storing device 150. For example, please referring to Table I, which shows the history list HL according to one embodiment. The current inputted parameter setting PMS1, i.e. [8, 2, 3, 3], and the current measured sleep qualities SQ1, i.e. 3.5, is recorded. Referring to FIG. 3, the measured sleep quality SQ1 is shown at the Score field.

TABLE I

| Measured sleep quality SQ1 | Inputted parameter setting PMS1 ([song, light intensity, sound volume, blue light reduction]) |
|---|---|
| 5.0 | [8, 3, 2, 2] |
| 5.0 | [7, 3, 2, 4] |
| 4.5 | [8, 3, 3, 2] |
| 4.0 | [1, 1, 2, 3] |
| 3.5 | [8, 2, 3, 3] |

Figure 4:
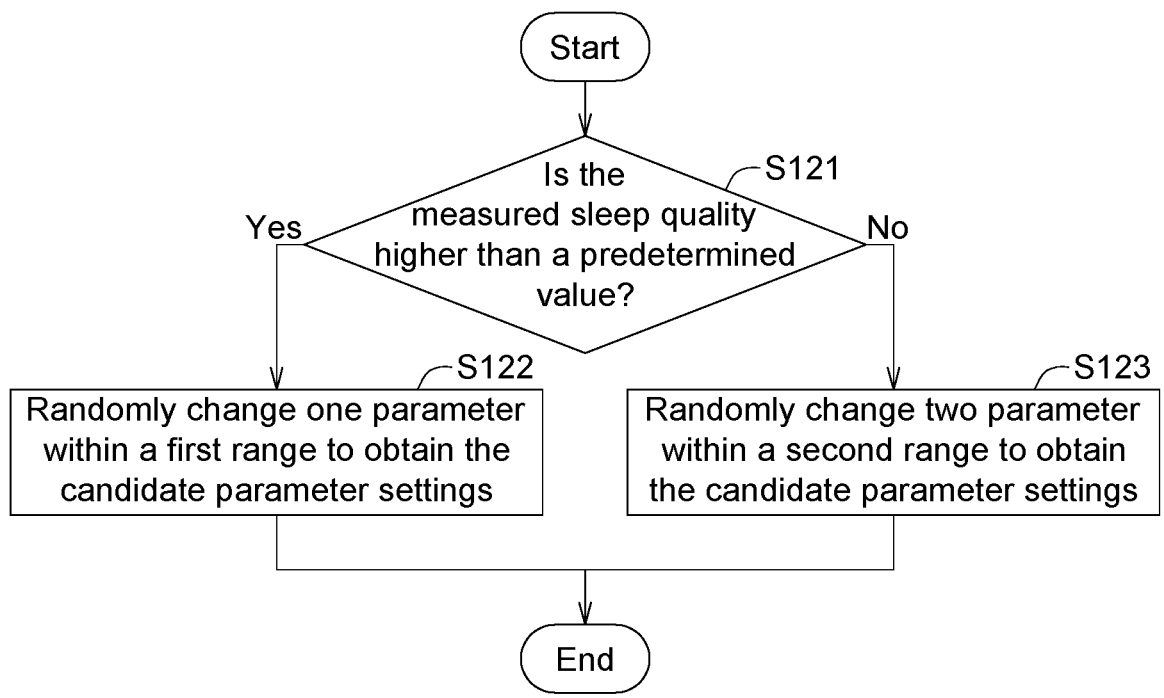
FIG. 4 shows a flowchart of the step S120 in the present disclosure.

Next, in step S120, the parameter learning module 113 of the processing device 110 generates a plurality of candidate parameter settings PMS2 according to the measure sleep quality SQ1. Please refer to FIG. 4, which shows a flowchart of the step S120 in the present disclosure. The step S120 is adopted a Reinforcement Learning technology to generate the candidate parameter settings PMS2. The step S120 includes steps S121 to S123. In step S121, the parameter learning module 113 determines whether the measured sleep quality SQ1 is higher than a predetermined value, such as 3.5, or not. If the measured sleep quality SQ1 is higher than the predetermined value, then the process proceeds to step S122; if the measured sleep quality SQ1 is not higher than the predetermined value, then the process proceeds to step S123.

In the step S122, one parameter is randomly changed within a first range, such as +1 to −1. If the measured sleep quality SQ1 is higher than the predetermined value, the current inputted parameter setting PMS1 is suitable for the user, and so the parameter in the inputted parameter setting PMS1 are only needed to slightly changed. For example, when the previous inputted parameter setting PMS0 is [1, 1, 2, 3], and the current inputted parameter setting PMS1 is [8, 2, 3, 3], one parameter in [8, 2, 3, 3] is randomly changed within +1 to −1, to obtain [8, 3, 3, 3], [8, 3, 3, 3] and [8, 2, 2, 3]. Then, [8, 2, 3, 3], [8, 3, 3, 3], [8, 3, 3, 3], [8, 2, 2, 3] and [1, 1, 2, 3] are the candidate parameter settings PMS2.

In step S123, two parameters are randomly changed within a second range, such as +3 to −3. If the measured sleep quality SQ1 is not higher than the predetermined value, the current inputted parameter setting PMS1 is not suitable for the user, and so the parameters in the inputted parameter setting PMS1 are is needed to greatly changed. For example, when the previous inputted parameter setting PMS0 is [1, 1, 2, 3] and the current inputted parameter setting PMS1 is [8, 2, 3, 3], two parameters in [8, 2, 3, 3] are randomly changed within +3 to −3 to obtain [8, 5, 1, 3], [8, 2, 1, 6] and [7, 2, 5, 3]. Then, [8, 2, 3, 3], [8, 5, 1, 3], [8, 2, 1, 6], [7, 2, 5, 3] and [1, 1, 2, 3] are the candidate parameter settings PMS2.

In the example of Table I and FIG. 3, the measured sleep quality SQ1 is "3.5", so the step S123 is performed and the candidate parameter settings PMS2 are "[8, 2, 3, 3], [8, 5, 1, 3], [8, 2, 1, 6], [7, 2, 5, 3] and [1, 1, 2, 3]."

Afterwards, in step S130, the sleep quality predicting module 112 of the processing device 110 generates a plurality of predicting sleep qualities SQ2 corresponding the candidate parameter settings PMS2. In this step, the sleep quality predicting module 112 searches the history list HL to generate the predicting sleep qualities SQ2. For example, one of the candidate parameter settings PMS2 may be "[8, 5, 1, 3]." By comparing with "[8, 5, 1, 3]", "[8, 3, 2, 2]" is the closet among all of the inputted parameter settings PMS1 in Table I, so "5.0" is deemed as the predicting sleep qualities SQ2. In one example, the candidate parameter settings PMS2 are "[8, 2, 2, 3], [8, 5, 1, 3], [8, 2, 1, 6], [7, 2, 5, 3] and [1, 1, 2, 3]," so the predicting sleep qualities SQ2 are "3.5, 5.0, 3.5, 3.5, 4.0."

Figure 5:
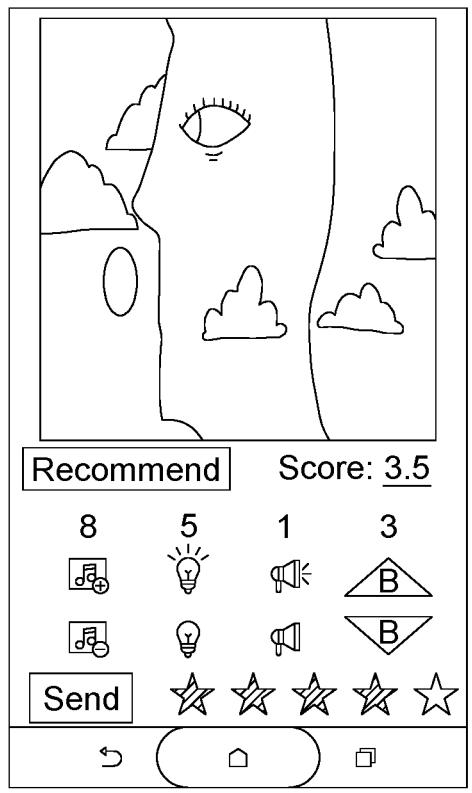
FIG. 5 shows the user interface indicating a recommending parameter setting in the present disclosure.

Then, in step S140, the parameter learning module 113 of the processing device 110 obtains the recommending parameter setting PMS3 by selecting one of the candidate parameter settings PMS2 according to the predicting sleep qualities SQ2. For example, one of the candidate parameter settings PMS2 corresponding the highest predicting sleep qualities SQ2 is selected to be the recommending parameter setting PMS3. In the example of Table I, the predicting sleep qualities SQ2 are "3.5, 5.0, 3.5, 3.5, 4.0", so the recommending parameter setting PMS3 is [8, 5, 1, 3] which corresponds the highest predicting sleep qualities SQ2, i.e. "5.0." Please referring to FIG. 5, the user interface 140 indicating the recommending parameter setting PMS3, i.e. [8, 5, 1, 3] in the present disclosure, is shown.

Figure 6A:
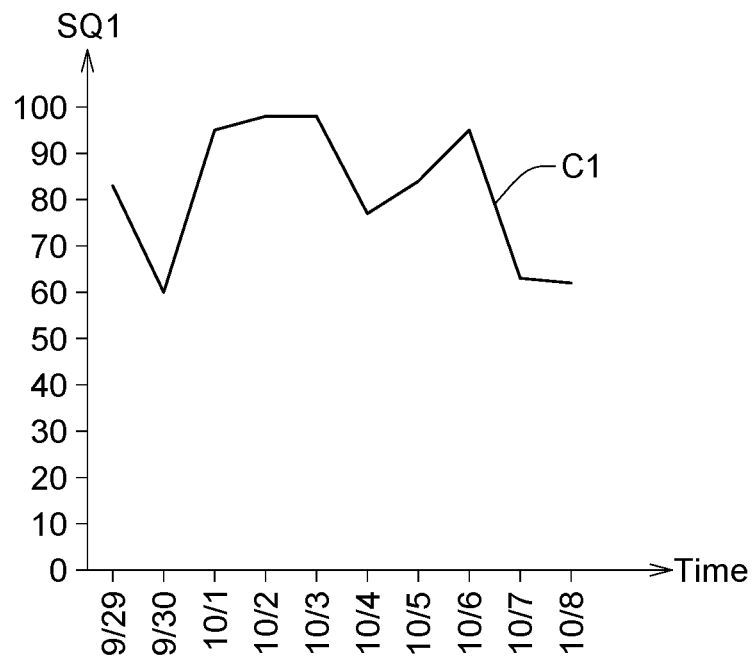
FIG. 6A shows a performance curve of a traditional sleep-aid device without performing the personalized parameter learning method in the present disclosure.
Figure 6B:
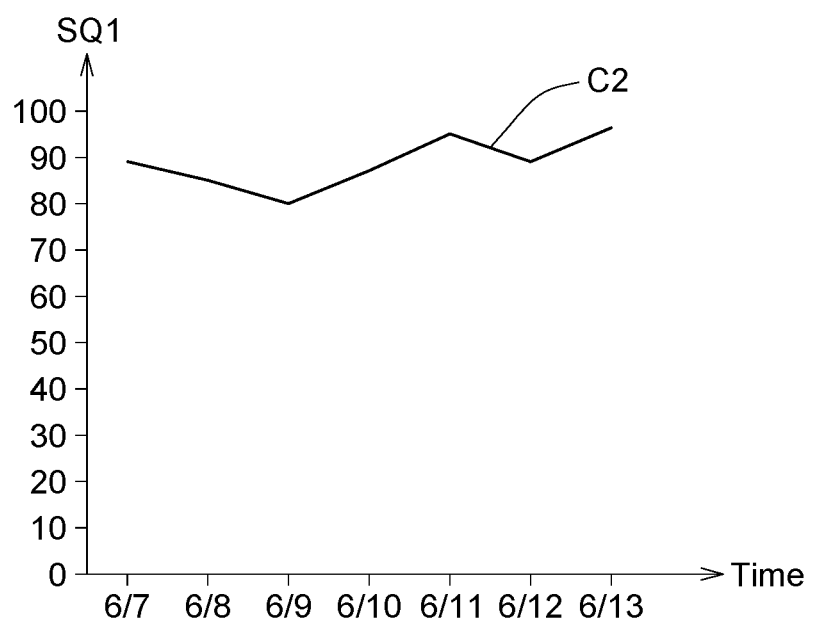
FIG. 6B shows a performance curve of the sleep-aid device performing the personalized parameter learning method in the present disclosure.

Please refer to FIG. 6A and FIG. 6B. FIG. 6A shows a performance curve C1 of a traditional sleep-aid device without performing the personalized parameter learning method in the present disclosure. FIG. 6B shows a performance curve C2 of the sleep-aid device 100 performing the personalized parameter learning method in the present disclosure. Table II is the performance data of the traditional sleep-aid device without performing the personalized parameter learning method. Table III is the performance data of the sleep-aid device 100 performing the personalized parameter learning method.

TABLE II

|  | measured sleep quality SQ1 | Total of the measured sleep qualities SQ1 of 7 days | Average of the measured sleep qualities SQ1 of 7 days | Standard deviation of the measured sleep qualities SQ1 of 7 days |
|---|---|---|---|---|
| September 29 | 83 | | | |
| September 30 | 60 | | | |
| October 1 | 95 | | | |
| October 2 | 98 | | | |
| October 3 | 98 | | | |
| October 4 | 77 | | | |
| October 5 | 84 | 595 | 85 | 13.74 |
| October 6 | 95 | 607 | 86.71 | 14.19 |
| October 7 | 63 | 610 | 87.14 | 13.26 |
| October 8 | 62 | 577 | 82.42 | 15.65 |
| Average | 81.5 | | | |
| Standard deviation | 15.36 | | | |

TABLE III

|  | measured sleep quality SQ1 | Total of the measured sleep qualities SQ1 of 7 days | Average of the measured sleep qualities SQ1 of 7 days | Standard deviation of the measured sleep qualities SQ1 of 7 days |
|---|---|---|---|---|
| June 7 | 89 | | | |
| June 8 | 85 | | | |
| June 9 | 80 | | | |
| June 10 | 87 | | | |
| June 11 | 95 | | | |
| June 12 | 89 | | | |
| June 13 | 96 | 621 | 88.71 | 5.56 |
| Average | 88.71 | | | |
| Standard deviation | 5.56 | | | |

It is clear that the average of the measured sleep qualities SQ1 of the performance curve C2 is higher than that of the performance curve C1. Further, the standard deviation of the performance curve C2 is lower than that of the performance curve C1. Therefore, by performing the personalized parameter learning method using the enhanced learning algorithm, an accurate recommendation of the parameter setting can be obtained, such that the sleep quality can be improved.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A personalized parameter learning method for a sleep-aid device, comprising:
    computing, by a processing device, a measured sleep quality of a user after operating the sleep-aid device with an inputted parameter setting at least according to a subjective feedback from the user;
    generating, by the processing device, a plurality of candidate parameter settings according to the measured sleep quality, wherein the inputted parameter setting is randomly changed to obtain the candidate parameter settings;
    generating, by the processing device, a plurality of predicting sleep qualities corresponding the candidate parameter settings; and
    obtaining, by the processing device, a recommending parameter setting by selecting one of the candidate parameter settings according to the predicting sleep qualities.

2. The personalized parameter learning method according to claim 1, wherein in the step of computing the measured sleep quality, the measured sleep quality is computed according to the subjective feedback from the user and an objective feedback form at least one sensor.

3. The personalized parameter learning method according to claim 2, wherein the sensor is a wearable device, a camera or a voice recorder.

4. The personalized parameter learning method according to claim 1, wherein in the step of generating the predicting sleep qualities, a history list recording a relationship between the measured sleep quality and the inputted parameter setting is searched.

5. The personalized parameter learning method according to claim 1, wherein in the step of generating the candidate parameter settings, if the measured sleep quality is higher than a predetermined value, one parameter in the inputted parameter setting is randomly changed to obtain the candidate parameter settings; if the measured sleep quality is not higher than the predetermined value, then two parameters in the inputted parameter settings are randomly changed to obtain the candidate parameter settings.

6. The personalized parameter learning method according to claim 1, wherein in the step of generating the candidate parameter settings, if the measured sleep quality is higher than a predetermined value, one parameter in the inputted parameter setting is randomly changed within a first range to obtain the candidate parameter settings; if the measured sleep quality is not higher than the predetermined value, then two parameters in the inputted parameter setting are randomly changed within a second range to obtain the candidate parameter settings; the first range is less than the second range.

7. The personalized parameter learning method according to claim 1, wherein one parameter of the inputted parameter setting is a song, a light intensity, a sound volume or a blue light reduction.

8. A sleep-aid device, comprising:
 a processing device, includes:
  a computing module for computing a measured sleep quality of a user after operating the sleep-aid device with an inputted parameter setting at least according to a subjective feedback from the user;
  a parameter learning module for generating a plurality of candidate parameter settings according to the measured sleep quality, wherein the inputted parameter setting is randomly changed to obtain the candidate parameter settings; and
  a sleep quality predicting module for generating a plurality of predicting sleep qualities corresponding the candidate parameter settings;
  wherein the parameter learning module is further for obtaining a recommending parameter setting by selecting one of the candidate parameter settings according to the predicting sleep qualities.

9. The sleep-aid device according to claim 8, wherein the computing module computes the measured sleep quality according to the subjective feedback from the user and an objective feedback form at least one sensor.

10. The sleep-aid device according to claim 9, wherein the sensor is a wearable device, a camera or a voice recorder.

11. The sleep-aid device according to claim 8, wherein the sleep quality predicting module is further for searching a history list recording a relationship between the measured sleep quality and the inputted parameter setting.

12. The sleep-aid device according to claim 8, wherein if the measured sleep quality is higher than a predetermined value, the parameter learning module randomly changes one parameter in the inputted parameter setting to obtain the candidate parameter settings; if the measured sleep quality is not higher than the predetermined value, then the parameter learning module randomly changes two parameters in the inputted parameter settings to obtain the candidate parameter settings.

13. The sleep-aid device according to claim 8, wherein if the measured sleep quality is higher than a predetermined value, the parameter learning module randomly changes one parameter in the inputted parameter setting within a first range to obtain the candidate parameter settings; if the measured sleep quality is not higher than the predetermined value, then the parameter learning module randomly changes two parameters in the inputted parameter setting within a second range to obtain the candidate parameter settings; the first range is less than the second range.

14. The sleep-aid device according to claim 8, wherein one parameter of the inputted parameter setting is a song, a light intensity, a sound volume and a blue light reduction.

15. A non-transitory computer readable medium storing a program causing a computer to execute a personalized parameter learning method, wherein the personalized parameter learning method comprises:
 computing a measured sleep quality of a user after operating a sleep-aid device with an inputted parameter setting at least according to a subjective feedback from the user;
 generating a plurality of candidate parameter settings according to the measured sleep quality, wherein the inputted parameter setting is randomly changed to obtain the candidate parameter settings;
 generating a plurality of predicting sleep qualities corresponding the candidate parameter settings; and
 obtaining a recommending parameter setting by selecting one of the candidate parameter settings according to the predicting sleep qualities.

* * * * *